(12) United States Patent
Tuschel et al.

(10) Patent No.: US 7,342,214 B2
(45) Date of Patent: *Mar. 11, 2008

(54) APPARATUS AND METHOD FOR CHEMICAL IMAGING OF A BIOLOGICAL SAMPLE

(75) Inventors: David Tuschel, Monroeville, PA (US); John S. Maier, Pittsburgh, PA (US)

(73) Assignee: Chemimage Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/433,650

(22) Filed: May 15, 2006

(65) Prior Publication Data

US 2006/0274301 A1 Dec. 7, 2006

Related U.S. Application Data

(63) Continuation of application No. 11/097,161, filed on Apr. 4, 2005, now Pat. No. 7,045,757, which is a continuation-in-part of application No. 11/045,081, filed on Jan. 31, 2005, now Pat. No. 7,060,955.

(51) Int. Cl.
*H01L 27/00* (2006.01)

(52) U.S. Cl. .................................. 250/208.1; 250/226

(58) Field of Classification Search ............ 250/208.1, 250/226, 216, 559.4, 559.44; 356/326, 328
See application file for complete search history.

(56) References Cited

U.S. PATENT DOCUMENTS

| | | | |
|---|---|---|---|
| 5,194,912 A | 3/1993 | Batchelder et al. |
| 5,377,003 A | 12/1994 | Lewis et al. |
| 5,377,004 A | 12/1994 | Owen et al. |
| 5,394,499 A | 2/1995 | Ono et al. |
| 5,442,438 A | 8/1995 | Batchelder et al. |
| 5,493,443 A | 2/1996 | Simon et al. |
| 5,528,393 A | 6/1996 | Sharp et al. |
| 5,623,342 A | 4/1997 | Baldwin et al. |
| 5,689,333 A | 11/1997 | Batchelder et al. |
| 5,710,626 A | 1/1998 | O'Rourke et al. |
| 5,784,162 A | 7/1998 | Cabib et al. |
| 5,862,273 A | 1/1999 | Pelletier |
| 5,866,430 A | 2/1999 | Grow |

(Continued)

FOREIGN PATENT DOCUMENTS

WO WO 95 11624 5/1995

OTHER PUBLICATIONS

Morris, Hoyt and Treado, "Imaging Spectrometers for Fluorescence and Raman Microscopy: Acousto-Optic and Liquid Crystal Tunable Filter," Applied Spectroscopy, vol. 48, No. 7, 1994.

(Continued)

*Primary Examiner*—Que T Le
(74) *Attorney, Agent, or Firm*—Duane Morris LLP

(57) ABSTRACT

In one embodiment, the disclosure relates to a method for determining illumination parameters for a stained sample, the method may include providing a stained sample and obtaining an absorption band of the sample; obtaining an emission band of the sample and determining the illumination parameters for the sample as a function of the absorption band and the emission band of the sample.

23 Claims, 5 Drawing Sheets

U.S. PATENT DOCUMENTS

| | | |
|---|---|---|
| 5,901,261 A | 5/1999 | Wach |
| 5,911,017 A | 6/1999 | Wach et al. |
| 5,943,122 A | 8/1999 | Holmes |
| 5,974,211 A | 10/1999 | Slater |
| 6,002,476 A | 12/1999 | Treado |
| 6,006,001 A | 12/1999 | Alfano et al. |
| 6,088,100 A | 7/2000 | Brenan et al. |
| 6,091,872 A | 7/2000 | Katoot |
| 6,222,970 B1 | 4/2001 | Wach et al. |
| 6,483,641 B1 | 11/2002 | MacAulay |
| 6,485,413 B1 | 11/2002 | Boppart et al. |
| 6,571,117 B1 | 5/2003 | Marbach |
| 6,690,466 B2 * | 2/2004 | Miller et al. ............. 356/326 |
| 6,697,665 B1 | 2/2004 | Rava et al. |

OTHER PUBLICATIONS

Morris, Hoyt, Miller and Treado, "Liquid Crystal Tunable Filter Raman Chemical Imaging," Applied Spectroscopy, No. 50, No. 6, Jun. 1996.

Skinner, Cooney, Sharma and Angel, "Remote Raman Microimaging Using an AOTF and a Spatially Coherent Microfiber Optical Probe," Applied Spectroscopy, vol. 50, No. 8, 1996.

* cited by examiner

APPARATUS AND METHOD FOR CHEMICAL IMAGING OF A BIOLOGICAL SAMPLE

The instant application is a continuation of application Ser. No. 11/097,161, filed Apr. 4, 2005 (now U.S. Pat. No. 7,045,757), which is a continuation-in-part of application Ser. No. 11/045,081, filed Jan. 31, 2005 (now U.S. Pat. No. 7,060,955) by the inventors named herein, the specifications of which are incorporated herein in their entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e., chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

Regardless of the type of optical equipment, a first step in any spectroscopic investigation is defining a suitable wavelength for illuminating the sample. The step of defining a suitable wavelength for illuminating the sample becomes even more important when simultaneous multiple images of the sample are sought. Conventional methods suggest illuminating a sample with a first wavelength (e.g., NIR or VIS) to obtain a first image, followed by illuminating the sample with a second wavelength to obtain a second image (e.g., Raman or dispersive Raman). Consequently, the conventional process is time consuming and is not suited for simultaneous imaging of the sample. There is a need for an apparatus and method for determining illumination parameters of a sample a priori of illuminating the sample.

The current disclosure addresses the need described above. In one embodiment, the disclosure relates to a method for obtaining a chemical image of a biological sample by providing a biological sample labeled with a Fluorophore; irradiating the sample with photons having wavelength within the illumination wavelength range; obtaining a spectral image of the sample; and generating a chemical image from the spectral image. The chemical image may define at least two spectral images of the sample obtained simultaneously. The spectral images can include a Raman image and a fluorescent image.

In another embodiment, an apparatus for obtaining a spectral image of a biological sample comprising means for determining a range of illumination wavelengths, the illumination wavelength interacting with the sample to simultaneously provide a first and a second spectra of the sample; a photon source for directing photons with a wavelength within the range to the sample, the illuminating photons interacting with the sample to produce interacted photons; a tunable filter for receiving interacted photons and forming a spectral image of the sample.

In still another embodiment, the disclosure relates to a system for obtaining multiple spectra of a biological sample. The system can include a processor programmed with instructions to determine illumination parameters of the sample as a function of the emission bandwidth of said sample; an illumination source for directing photons having a wavelength within the illumination parameters of the sample, the illuminating photons interacting with the sample to provide interacted photons; and a tunable filter for receiving the interacted photons from the sample and providing at least a first and a second spectra of the sample.

DETAILED DESCRIPTION

The disclosure generally relates to a method and apparatus for determining illumination parameters for a sample. Having an a priori knowledge of an optimal illumination parameters (e.g., optimal illumination wavelength range) for obtaining spectral images of a sample is particularly important in that the optimal illumination parameter enables simultaneous detection of more than one spectra of the sample. The optimal illumination parameters can also be used with different detection modes such as: wide field, Raman chemical imaging, multipoint, dispersive single point and dispersive line.

Figure 1:
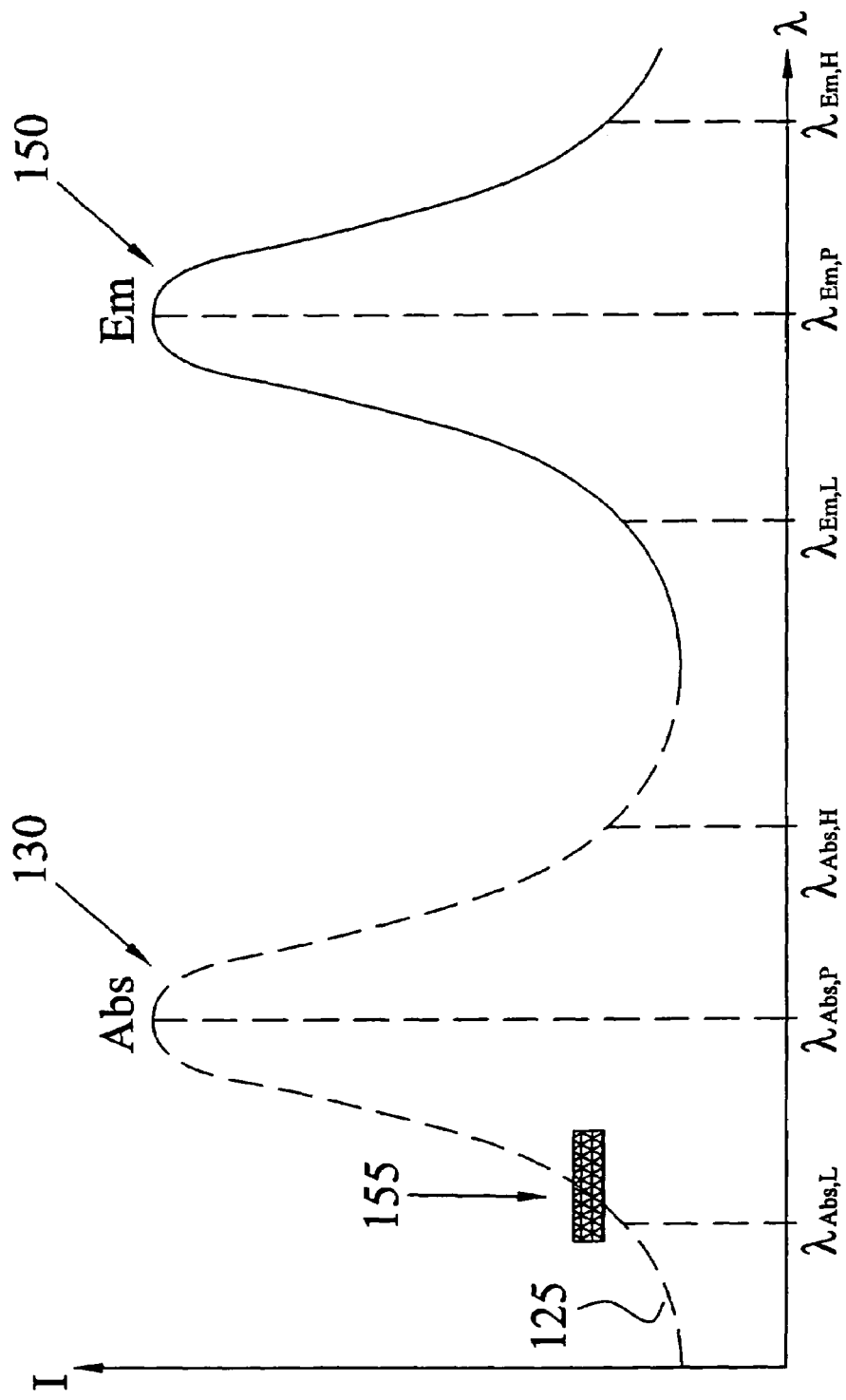
FIG. 1 graphically illustrates the relationship between intensity and wavelength of a sample.

FIG. 1 graphically illustrates the relationship between intensity and wavelength of a sample. The method of obtaining absorption and emissivity bands are conventionally known. It is also known that emissive energy is associated with fluorescent imaging and absorption energy is associated with near infrared ("NIR") energy. Thus, as a first step a sample may be illuminated with photons of different frequencies (interchangeably, detection photons or illumination photons) to determine the sample's absorption and emission wavelengths.

In FIG. 1, line 125 represents the energy absorption relationship of a sample exposed to detection photons. Peak 130 indicates the peak wavelength ($\lambda_{Abs, P}$) for absorption spectrum of the sample; peak 140 indicates the peak wavelength for the emission spectrum ($\lambda_m$) of the sample and peak 150 shows the peak Raman intensity occurs at ($\lambda_{H, P}$). A range of wavelength were absorption energy of the sample can be detected is shown to extend from $\lambda_{abs-L}$ to $\lambda_{abs-H}$. Similarly, a range of wavelength were emissive energy of the sample can be detect extends from $\lambda_{Em-L}$ to $\lambda_{Em-H}$.

As will be discussed in greater detail, according to one embodiment of the disclosure, an optimal wavelength for multi-spectral imaging can occur at a wavelength just below or about $\lambda_{abs-L}$. Thus, a method is disclosed for defining illumination parameters which includes (i) defining a range of absorption wavelengths for the sample; (ii) defining a range of emission wavelengths for the sample; and (iii) assessing a suitable illumination parameters for the sample as a function of the absorption wavelength and the emission wavelength. These steps can be implemented sequentially or simultaneously. By way of example, the region shown as 155 in FIG. 1 shows a possible illumination wavelength such that it is shorter than the wavelength of a peak in the emission spectrum. The illumination parameters may also be used to define a illumination laser line or a suitable Raman illumination wavelength. Since wavelength and frequency are inversely proportional, steps (i)-(iii) can be implemented and defined in view of a frequency band. That is, in view of a range of absorption wavelengths of a sample an equivalent frequency bandwidth for the sample can be defined.

In another embodiment of the disclosure, a method for determining illumination parameters for a sample includes: simultaneously illuminating the sample with illuminating photons. The illuminating photons can have several different wavelengths or define a broad range of wavelengths. Next, the emissive and absorption wavelengths for the sample can be defined. Alternatively, the sample's bandwidth for emission and absorption can be determined. The emission and the absorption bands can also define the peak intensity wavelength as well as the lower and the upper wavelength ranges for each band. Using the lower wavelength of the absorption band ($\lambda_{abs-L}$) as a starting point, an optimal Raman wavelength detection wavelength for the sample can be defined as Raman scattered photons having wavelength about or below $\lambda_{abs-L}$. By way of example, one such region is shown as region 155 in FIG. 1. The illumination parameters thus obtained can be used to illuminate the sample with illuminating photons of different wavelengths to obtain simultaneous spectral images of the sample. The illuminating photons can be provided by a laser line, wide-field, Raman chemical imaging, multipoint imaging, dispersive single point and dispersive lines specifically devised to be within the desired wavelength range.

FIGS. 2A-2G each schematically illustrate spectral images of a sample receiving different excitation wavelengths. More specifically, FIGS. 2A-2G depict absorption, emission and Raman spectra for a biological sample stained with a die and a method for determining illumination parameters for the sample in view of absorption and emission spectra of the sample. In one embodiment of the disclosure the die is a Flourophor. Suitable Fluorophore stains include an immuno-fluorescent compound, a basophilic compound, an acidophilic compound, neutral stains and naturally occurring luminescent molecules. Once stained, the sample can be irradiated with photons having a wavelength within the illumination wavelength range in order to obtain the spectral images of the sample.

Figure 2A:
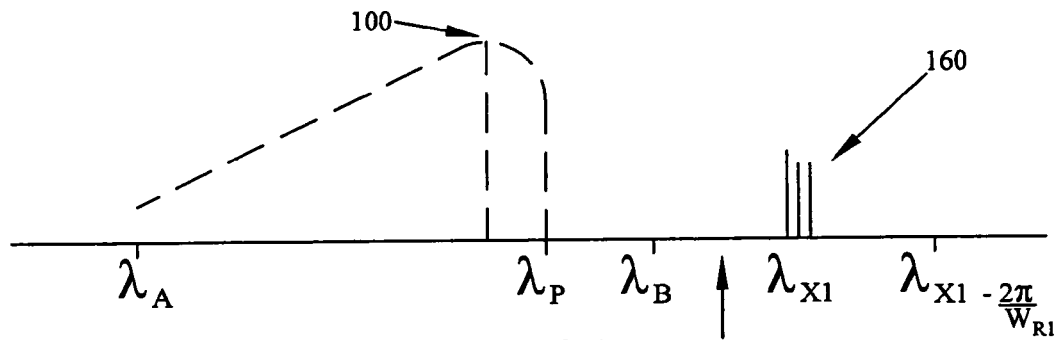
FIGS. 2A-2G each schematically illustrate spectral images of a sample receiving different excitation wavelengths.

In FIG. 2A, peak 100 shows the emission peak for the stained sample. As is conventionally known, the emission bandwidth (or its equivalent range of wavelength) is a property of the material. In FIG. 2A, the emission range spans between $\lambda_A$-$\lambda_B$, with a peak emission wavelength occurring at $\lambda_p$. The illumination (excitation) wavelength is arbitrarily set at $\lambda_{X1}$. Raman peaks are identified as peaks 160. Raman peaks are shifted from excitation wavelength ($\Delta\lambda_{X1}$) by a fixed wavelength which is commensurate with the energy lost due to Raman vibration. Increasing or decreasing the excitation wavelength will have a direct effect on the wavelength where the Raman peaks occur. This is schematically illustrated in FIGS. 2A-2G where changing the excitation energy from the wavelength $\lambda_{X1}$ to $\lambda_{X7}$ results in shifting the wavelength where Raman peaks 160 occur. Referring again to FIG. 2A, the Raman peaks 160 occur at wavelength $\lambda_{X1}$-$1/\psi$; where $\psi$ is the Raman energy loss due to Raman excitation expressed in wavenumbers and can be quantified as $$\psi = (1/2\Pi c)(k/\mu)^{1/2};$$

where k is the chemical bond force constant, c is the speed of light, and $\mu$ is the reduced mass of the molecular oscillator.

Figure 2B:
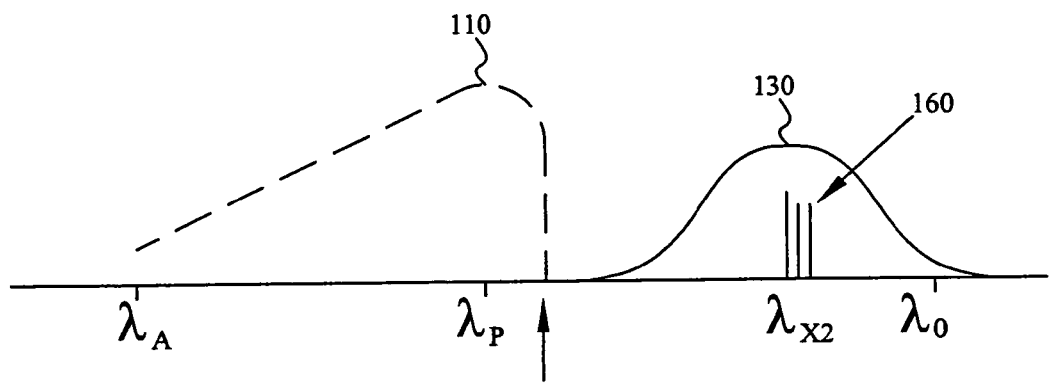
Figure 2C:
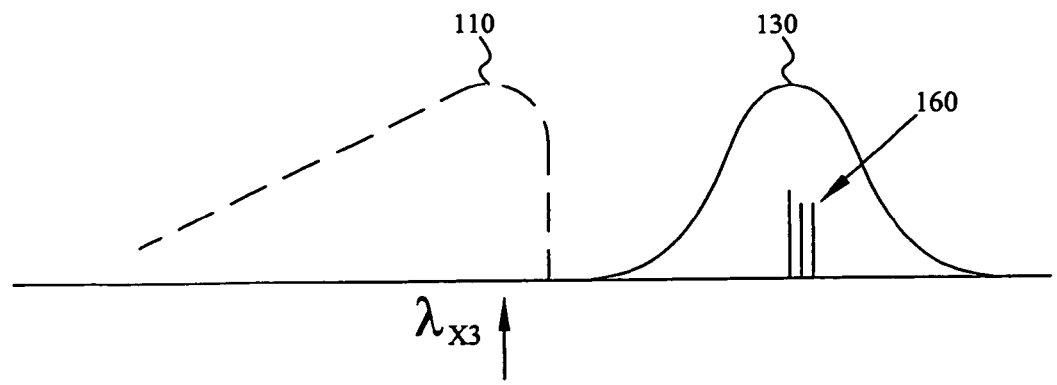

In FIGS. 2B and 2C, peak 110 represents the emission peak and peaks 160 represent Raman scattering peaks for the sample under study. Peak 130 illustrates the sample's Fluorescence spectrum. In FIGS. 2B and 2C the excitation wavelength is set to $\lambda_{X2}$ and $\lambda_{X3}$, respectively, such that the Fluorescent spectrum of the sample occurs at a wavelength near the excitation region as shown. As can be seen from FIGS. 2B and 2C, the sample's Fluorescence spectrum overlaps with the Raman peaks 160, which as stated, occurs at a fixed wavelength from the excitation wavelength. The overlap makes spectral analysis difficult, if not impossible, as the Raman signals will become overwhelmed by the Fluorescent signals.

Figure 2D:
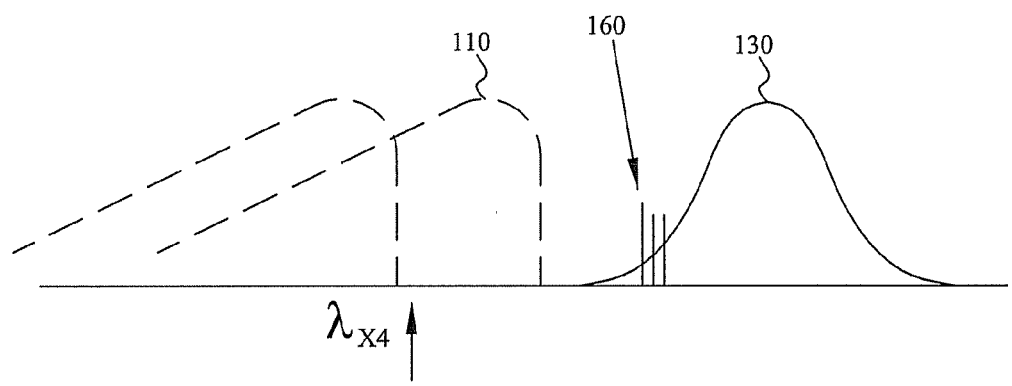

In contrast, the illumination parameter $\lambda_{X4}$ in FIG. 2D is selected such that Raman peaks 160 occur just below the onset of Fluorescent spectrum 130. Here, each of the Raman 160, Fluorescence 130 and Emission 110 spectra are visible within a narrow range of wavelengths and can be detected substantially simultaneously with a single detection device.

Figure 2E:
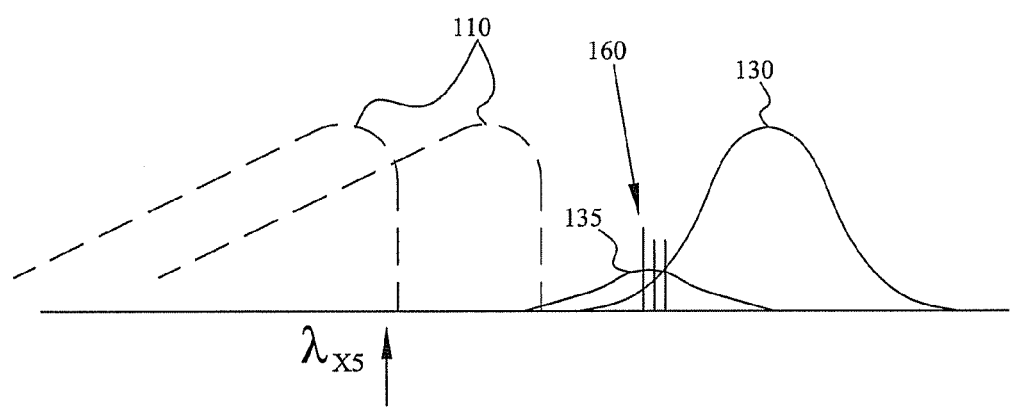

In FIG. 2E, the sample has dual Fluorescence peaks 130 and 135. Fluorescence peak 135 defines a lower intensity peak as compared with Fluorescence peak 130. Signals from the Raman peaks 160 may be more easily detectable over Fluorescent signal indicating peak 135. In FIG. 2E, illumination wavelength $\lambda_{X5}$ is selected such that Raman peaks 160 overlap with the Fluorescence peak 135. However, since the Raman signals have a higher intensity, Raman peaks 160 may be identified from emission spectrum 135.

Figure 2F:
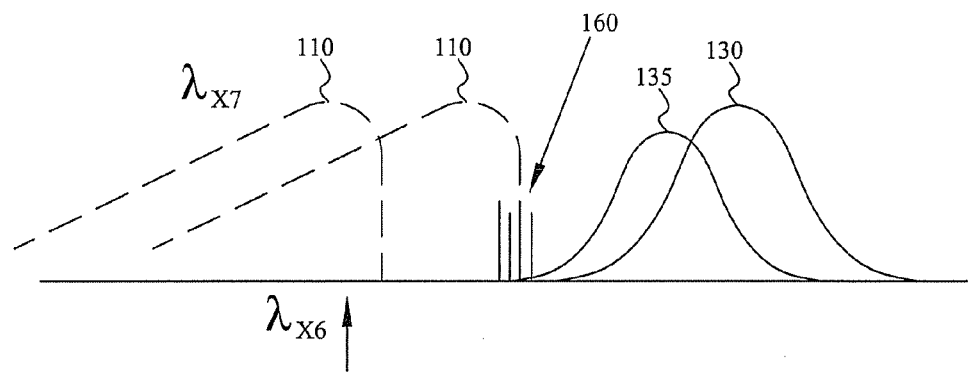
Figure 2G:
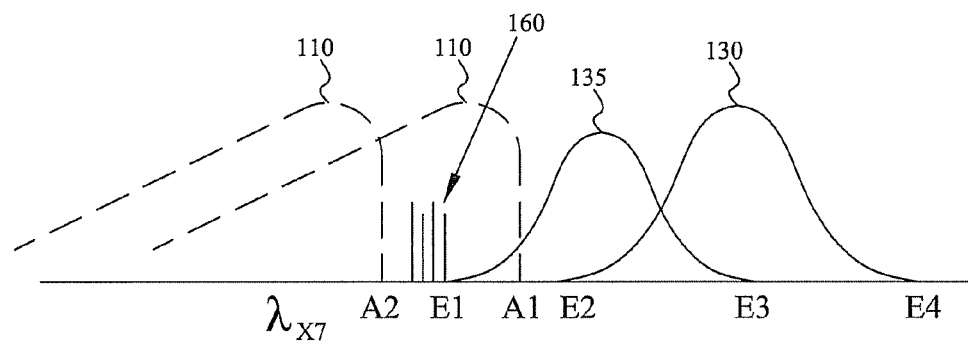

In FIG. 2F the excitation wavelength is shifted to $\lambda_{X6}$ and Raman Peaks 160 are no longer eclipsed by Fluorescent peaks 130 and 135. The Raman signals may nonetheless receive interference from emission spectrum of peak 110. Since at least a portion of Raman peaks 160 falls between Fluorescent peak 135 and emission peak 110, the Raman signal may be at least partially distinguishable. In FIG. 2G, excitation wavelength $\lambda_{X7}$ is shifted to a lower wavelength resulting in the shifting of Raman peaks 160. Here, emission peaks 110 overlap Raman peaks 160 rendering the Raman signals indistinguishable from the emission signals.

As can be seen from FIGS. 2A-2G, the excitation wavelength can be selected such that at least two spectra of the sample are simultaneously visible within a narrow range of wavelengths. According to one embodiment of the disclosure the excitation wavelength is soleelod such that Raman peaks appear at a wavelength substantially free from interference from other signals. According to another embodiment, the excitation wavelength can be selected such that signals from Raman peaks are distinguishable from signals depicting emission or Fluorescence spectra. According to still another embodiment of the disclosure, the excitation wavelength is selected such that an imaging device can simultaneously capture the Fluorescence emission as well as the Raman spectra for the sample. In still another embodiment of the disclosure, the excitation wavelength is selected such that an imaging device can simultaneously capture the Fluorescence emission as well as the Raman spectra for the sample.

In one embodiment of the disclosure, an apparatus is provided to assess the illumination parameter for a histologically labeled sample. The sample can be labeled with a conventional identifier, such as a Fluorophore substance. Next, an illumination parameter defining a suitable illumination wavelength can be selected such that both the emission peak and Raman scattering peaks can be detected with one imaging apparatus. The imaging apparatus may include gathering optics (e.g., optical trains for collecting photons emitted, Raman scattered, transmitted, or reflected from the sample), one or more tunable filters (e.g., liquid crystal tunable filter (LCTF), Acousto-optical Tunable Filter (AOTF) or fiber array spectral translator). A charged-coupled device or other suitable camera or recording medium may be coupled to the imaging apparatus in order to capture the spectra.

In a system according to an embodiment of the disclosure, the illumination parameter for a sample includes one or more illumination sources, an optical train and a processor programmed with instructions to simultaneously illuminate the sample with illuminating photons and detect an emission band and an absorption band of the sample. The instructions can also include defining a lower wavelength range and an upper wavelength range for the band and determine the illumination parameters for the sample as a function of the absorption and the emission bands of the sample. Finally, the instructions may include defining a suitable Raman wavelength for the sample at a wavelength shorter than the lower wavelength range ($\lambda_{EM, L}$) of the emission spectrum.

Figure 3:
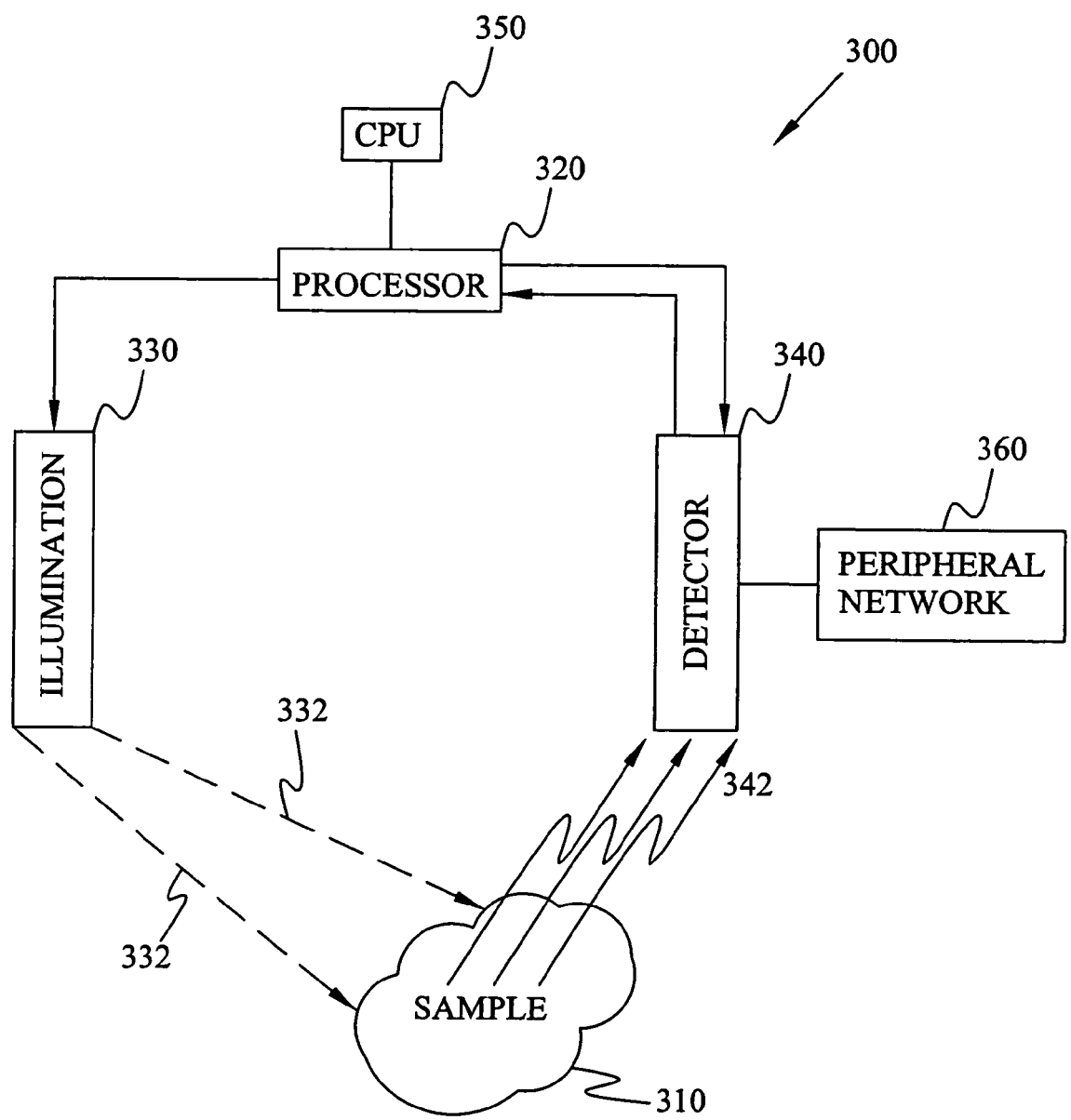
FIG. 3 is a functional diagram of a system according to one embodiment of the disclosure.

FIG. 3 is a functional diagram of a system according to one embodiment of the disclosure. In FIG. 3, system 300 is devised to obtain and analyze chemical images of sample 310. Sample 310 can be any biological, organic or inorganic sample suitable for histological studies. Illumination source 330 is positioned to provide excitation photons 332 to sample 310. Illumination source 330 can be positioned above, near or below the sample. Excitation photons 332 define excitation wavelengths which can cover a broad range of spectra (e.g., $\lambda_{X1}$-$\lambda_{X7}$). Moreover, illumination source 330 can be adapted to change excitation wavelengths based on instructions communicated by Processor 320. Detector 340 is positioned near sample 340 to receive interacted photons 342. Interacted photons 342 may include Fluorescence, reflection, absorption, transmission, emission and Raman photons. Interacted photons can be received and collected by Detector 340 which may include electro-optical devices suitable for gathering and analyzing photons of broad wavelengths. Detector 340 may include, for example, an optical train for gathering and focusing interacted photons; one or more optical filters for rejecting photons of undesired wavelengths; an LCTF for obtaining spectral images of Sample 310; and a charge-coupled device for devising a chemical image based on the spectral images of Sample 310. Detector 340 can communicate with peripheral network devices 360 such as printers, video recorders or internet communication systems.

Processor 320 can receive spectral images of the sample from Detector 340 and determine whether the illumination wavelength should be changed. For example, if Detector 340 devises a spectral image of a sample similar to FIG. 2C, processor 320 can determine that Raman signals from peaks 160 are indistinguishable from Fluorescent signal 130. Based on this determination, processor 320 can direct a change in excitation wavelength produced by illumination source 330 such that signal interference is reduced to that shown in FIG. 2D. Processor 350 can also communicate with CPU 350 to receive executable instructions or to access a database of related information such as the chemical identifier or the properties of the Fluorophore used on sample 310. CPU 350 can be used to communicate additional information to the processor.

After one or more iterations, Processor 320 can determine the optimal illumination parameter for the sample such that more than one spectral image can be detected simultaneously. The spectral image of the sample can be used to define one or more chemical images of the sample and to identify the sample under study. Such analysis can be implemented using a single detection and identification system and lends substantial efficiency to histological analysis.

While the principles of the disclosure have been disclosed in relation to specific exemplary embodiments, it is noted that the principles of the invention are not limited thereto and include all modification and variation to the specific embodiments disclosed herein.

The invention claimed is:

1. An apparatus for simultaneously obtaining spectral images of a biological sample comprising:
    means for determining a range of illumination wavelengths, where illuminating photons having a wavelength in the illumination wavelength range interact with the sample to thereby provide interacted photons for simultaneously forming a first spectral image and a second spectral image of the sample;
    a photon source for directing said illuminating photons to the sample to thereby produce said interacted photons; and
    a tunable filter for receiving said interacted photons to thereby enable the formation of said first and said second spectral images of the sample.

2. The apparatus of claim 1, wherein the first and the second spectral image of the sample are formed from the same interacted photons.

3. The apparatus of claim 1, wherein the first spectral image is a Raman spectral image.

4. The apparatus of claim 1, wherein the second spectral image is a Fluorescent spectral image.

5. The apparatus of claim 1, the apparatus further comprising a rejection filter for filtering the photons from the photon source.

6. The apparatus of claim 1, the apparatus further comprising a rejection filter for filtering interacted photons.

7. The apparatus of claim 1, the apparatus further comprising an objective lens for collecting interacted photons and directing the interacted photons to the tunable filter.

8. The apparatus of claim 1, wherein the tunable filter is selected from the group consisting of LCTF, AOTF and fiber array spectral translator.

9. The apparatus of claim 1, wherein the spectral images of the sample include at least one of a fluorescent signal and a Raman signal.

10. The apparatus of claim 1, wherein the sample further comprises a fluorophore substance.

11. The apparatus of claim 1, wherein the means for determining a range of illumination wavelengths further comprises means for defining a fluorescence emission peak for the sample and means for selecting a range of wavelengths below the emission peak as said range of illumination wavelengths.

12. The apparatus of claim 1, wherein the means for determining a range of illumination wavelengths further comprises means for defining a fluorescent bandwidth for the sample and means for selecting a range of wavelengths overlapping the fluorescent bandwidth as said range of illumination wavelengths.

13. The apparatus of claim 1, wherein the illumination wavelength range overlaps a region of an emission bandwidth.

14. A system for obtaining multiple spectra of a biological sample comprising:
    a processor programmed with instructions to determine illumination parameters of the sample as a function of an emission bandwidth of said sample, the illumination parameters providing a range of wavelengths for illuminating photons to thereby enable obtaining a first and a second spectra of the sample simultaneously;

an illumination source for directing said illuminating photons towards the sample to interact with the sample to thereby provide interacted photons; and a tunable filter for receiving said interacted photons from the sample to thereby enable the formation of at least the first and the second spectra of the sample.

15. The system of claim 14, wherein the first spectrum is a fluorescence spectrum of the sample.

16. The system of claim 14, wherein the first spectrum is an absorption spectrum of the sample.

17. The system of claim 14, wherein the second spectrum is a Raman spectrum of the sample.

18. The system of claim 14, wherein the illumination source further comprises a rejection filter.

19. The system of claim 14, the system further comprising an optical lens for collecting and directing the interacted photons to the tunable filter.

20. The system of claim 14, wherein the tunable filter is selected from the group consisting of LCTF and AOTF.

21. The system of claim 14, wherein the illumination parameters define a waveband where at least two spectra of the sample are inclusively detectable.

22. The apparatus of claim 1, further comprising a processor for generating a chemical image identifying the composition of the sample from the spectral images.

23. The system of claim 14, wherein the processor has further programmed instructions for generating a chemical image identifying the composition of the sample from at least the obtained first and second spectra.

* * * * *